(12) United States Patent
Kumar

(10) Patent No.: US 10,933,057 B2
(45) Date of Patent: Mar. 2, 2021

(54) SYNERGISTIC COMPOSITIONS AND DEVICES FOR GYNECOLOGICAL PROCEDURES

(71) Applicant: Pathyil Damoderam Krishna Kumar, Palakkad (IN)

(72) Inventor: Pathyil Damoderam Krishna Kumar, Palakkad (IN)

( * ) Notice: Subject to any disclaimer, the term of this patent is extended or adjusted under 35 U.S.C. 154(b) by 252 days.

(21) Appl. No.: 16/026,684

(22) Filed: Jul. 3, 2018

(65) Prior Publication Data

US 2019/0000825 A1    Jan. 3, 2019

(30) Foreign Application Priority Data

Jul. 3, 2017 (IN) ............................. 201741023289
Jul. 3, 2017 (IN) ............................. 201741023333

(51) Int. Cl.
| | |
|---|---|
| A61B 17/42 | (2006.01) |
| A61K 31/4468 | (2006.01) |
| A61B 1/32 | (2006.01) |
| A61P 29/00 | (2006.01) |
| A61L 31/00 | (2006.01) |
| A61K 31/215 | (2006.01) |
| A61M 29/00 | (2006.01) |
| A61B 10/00 | (2006.01) |
| A61M 31/00 | (2006.01) |

(52) U.S. Cl.
CPC ............ *A61K 31/4468* (2013.01); *A61B 1/32* (2013.01); *A61B 10/0045* (2013.01); *A61B 17/42* (2013.01); *A61K 31/215* (2013.01); *A61L 31/005* (2013.01); *A61M 29/00* (2013.01); *A61P 29/00* (2018.01); *A61B 2010/0074* (2013.01); *A61B 2017/4225* (2013.01); *A61B 2217/005* (2013.01); *A61B 2217/007* (2013.01); *A61M 31/00* (2013.01)

(58) Field of Classification Search
CPC ........... A61B 17/42; A61B 1/32; A61M 29/00
See application file for complete search history.

(56) References Cited

U.S. PATENT DOCUMENTS

| | | | | |
|---|---|---|---|---|
| 2,832,343 | A | * 4/1958 | Mose ....................... | A61D 1/02 604/104 |
| 3,866,601 | A | * 2/1975 | Russell .............. | A61B 1/00142 600/114 |
| 3,882,852 | A | 5/1975 | Sinnreich | |

(Continued)

FOREIGN PATENT DOCUMENTS

WO    2014/205351    12/2014

OTHER PUBLICATIONS

Indian Patent Office; International Search Report and Written Opinion dated Sep. 4, 2018; 10 pages.

*Primary Examiner* — Alexander J Orkin
(74) *Attorney, Agent, or Firm* — Sunstein LLP

(57) ABSTRACT

Synergistic compositions and medical devices for use in treatment during gynecological procedures are provided. A gynecological device for treatment of cervical blockages without general anesthesia thereby suitable for out-patient service, saving time and money to the patients is provided. Synergistic compositions that enable the practioners to perform gynecological procedures without pain or bleeding to the patients are provided.

19 Claims, 11 Drawing Sheets

(56) References Cited

U.S. PATENT DOCUMENTS

| | | | |
|---|---|---|---|
| 2007/0066990 A1* | 3/2007 | Marsella | A61M 29/02 606/193 |
| 2007/0106174 A1* | 5/2007 | Sanders | A61B 10/0291 600/563 |
| 2013/0041398 A1* | 2/2013 | Goddard | A61M 29/00 606/191 |
| 2014/0200591 A1* | 7/2014 | Sullivan | A61B 17/42 606/119 |
| 2018/0132896 A1* | 5/2018 | Begg | A61B 1/32 |

* cited by examiner

3c

3b

3a (a)

(b)

SYNERGISTIC COMPOSITIONS AND DEVICES FOR GYNECOLOGICAL PROCEDURES

CROSS REFERENCE

This application claims priority to Indian Application No. 201741023289 and Indian Application No. 201741023333, both filed on Jul. 3, 2017, herein incorporated by reference in their entirety.

TECHNICAL FIELD

Illustrative embodiments of the invention generally relates to the field of pharmaceutical chemistry and medical devices for use in gynecological procedures.

BACKGROUND ART

Annual wellness visit to gynecologists are recommended for women throughout the world in order to maintain their reproductive health. The most common exam performed by a gynecologist is a speculum examination to analyze the cervix. The practioner may also choose to perform colposcopy to better assess the health of the cervix if abnormal cells are spotted during a pap smear test or if there is recurrent bleeding after intercourse or severe vaginal discharge or intermenstrual bleeding is observed in patients. A colposcope is essentially a mounted binocular microscope used during colposcopy.

In some cases, women dread going to gynecologists due to the intense pain and discomfort experienced during the pelvic examinations. Many women experience bleeding during gynecological procedures. Currently, most medical procedures in the field of gynecology and reproductive medicine such as intra-uterine insemination (IUI), artificial fertilization, cervical biopsy, colposcopy or endometrial ablation are typically performed with the use of general anesthesia. The patient under general anesthesia stays unconscious for a long time even after the completion of the procedure. General anesthesia requires the presence of an anesthesiologist and hospital admission which often translates into increased costs for the patient.

Gynecologists specializing in reproductive medicine often encounter cervical blockage as one of the reasons in patients with difficulty in conceiving a child. Cervical stenosis or cervical blockage is a condition in which the cervix narrows or completely closes off, hindering or blocking the passage between the uterus and the vaginal canal. Cervical stenosis can exist at birth as a result of a genetic condition, or it can develop due to endometrial cancer, invasive cervical surgeries, cervical trauma or cervical/vaginal atrophy due to menopause. Cervical blockage can interfere with sperm getting to the egg and complicate fertility treatments like insemination or in vitro fertilization. Cervical blockage must be removed to ensure successful fertility treatments. Most of the medical devices used by gynecologists around the world for treating cervical blockage requires the use of general anesthesia and often requires hospital admission which again results in increased costs for patients.

U.S. Pat. No. 6,860,235 B2, discloses an apparatus for creating a pathway in an animal for applications such as artificial insemination (AI), useful in association with a catheter having a tube coupled to a membrane initially positioned substantially inside the tube.

US 2018/0014965, provides a medical device for measuring and/or providing cervical dilation including an elongate body defining a proximal end and a distal end, as well as an expandable element coupled to the distal end of the elongate body. An array of movable elements may be disposed circumferentially about the elongate body, where the array of movable elements is movably coupled to the distal end of the elongate body by a plurality of wires. The medical device may further include a measurement mechanism able to determine a radial spacing of the array of movable elements, as well as a dilation indicator in communication with the measurement mechanism. One or more pressure sensors may be coupled to the array of movable elements, whereby a control element is in communication with the pressure sensors. In addition, an inflation source may be included in fluid communication with the expandable element.

WO 2014/093332 discloses methods and apparatus for speeding the softening of the cervix (cervical ripening) by way of application of ultrasound energy. A vaginal transducer may be used to emit pulse-modulated ultrasound energy directed to the cervix. Focused ultrasound energy may be applied trans-abdominally and directed at the cervix. Ultrasound energy is widely used in medical applications such as diagnostic imaging, therapeutic heating and non-invasive surgery.

Wang Dong-hong and Xin Yi-jun (Lanzhou Anning District Wanli Hospital, Lanzhou 730020, Gansu Province, China) in their article titled "Anesthetic effect of propofol combined with fentanyl and misoprostol for artificial abortion" (Chinese Journal of Healthy birth and child care, 2013-01) tried to optimize the utilization of propofol in anesthesia schedule for artificial abortion. Patients received (propofol+fentanyl+misoprostol group) misoprostol 400 μg at the posterior fornix 2 hours before operation and then 0.05 mg fentanyl and 2 mg/kg propofol.

Pan Li-li et al. investigated the clinical effect of oral misoprostol regimen before painless artificial abortion in "*Preoperative oral misoprostol for painless artificial abortion*" (Chinese Journal of Healthy birth and child care, 2013-01). The study compared to routine painless abortion under ibuprofen and fentanyl combined anesthesia, the intervention group took misoprostol with a dose of 400 μg an hour before anesthesia.

MIMS Malaysia prescribes Fentanyl dosage as 50-100 mcg (1-2 ml) for Adults, 25-50 mcg/kg (0.5-1 ml) for elderly and poor risk patients, 50-100 mcg/kg (1-2 ml) for the control of pain in post-operative patients, and for children (2-12 years) 20-30 mcg/kg (0.4-0.6 ml/10 Kg).

WO/2007/131687 discloses the use of *Plantago ovata* (husk) in the preparation of a drug intended for the treating Parkinson's disease, specifically in the preparation of a co-adjuvant drug of the action of the active principle L-dopa. The disclosure also relates to pharmaceutical compositions and preparations which comprises *Plantago ovata* and at least L-dopa.

WO/2010/003805 discloses the use of *Plantago ovata* seed husk in the form of a pharmaceutical composition comprising pharmaceutically accepted additives and, rich in mucilages, for the preparation of a medicament for the reduction of the number of Aberrant Crypt Foci (ACF) in the colon of patients diagnosed with intestinal polyps and for the prevention of colon cancer.

SUMMARY OF THE EMBODIMENTS

The Illustrative embodiments of the present invention provide a dilating device to clear cervix pathway, suitable for out-patient service, save time and cost to the patient. The device comprises four parts (1) a shaft, (2) a hollow cylinder or a connecting part covering the shaft, (3) a base or handle part, and (4) a taper part to precede the middle part with provision(s) on its external surface to connect with a patch. The shaft (1) having a head (1a) at one end and threaded part (1c) to connect at the other end. From head to threaded end of the shaft, bears a minimum of one passage bore (1d) to accommodate any fluid transmission, optic fiber cables, light sources, camera connectivity, probes or surgery related equipment/purpose including draining of liquids and optionally a separate drain provision to remove any undesired liquid, during the procedure.

The illustrative embodiments of the present invention provide a synergistic a drug combination of fentanyl and misoprostol. In a preferred embodiment, the combined drugs are used for application at the vaginal mucosa in the form of a gel or pessary before any uterine procedure.

In some embodiments of the invention, provided is a dilating device for unblocking cervix pathway, comprising the following parts: (a) a shaft with a head at one end and a threaded part at the other end, (b) a tubular structure as middle or connecting part covering the shaft, (c) a base or handle part, (d) a taper part to precede the middle part with provision(s) on its external surface to connect with a patch and (e) a *Plantago ovata* cone or patch.

In some embodiments of the invention the central part of the shaft of the device between the head and the threaded part is unthreaded. In some embodiments of the invention the central part of the shaft comprises a plurality of bores. In some embodiments of the invention the bores in the central part of the shaft comprise one or more detection systems, flushing systems, and/or drainage systems In some embodiments of the invention the central part of the shaft comprises at least one bore in the center or around the center. In some embodiments of the invention the central part of the shaft (1) comprises means for fluid transmission, a light source, a fluorescent probe, camera connectivity, a surgical probe, a drain provision to remove any undesired liquid, during the procedure.

In some embodiments of the invention the central part of the shaft is covered by a tubular structure, to connect the taper part and base or handle part of the device having a smooth external surface and is provided with a horizontal pore sufficient enough to allow the shaft to pass through.

In some embodiments of the invention the base or handle part is tubular inside with a threaded part and an unthreaded part, having external side tapered towards the head of the shaft, with wider portion at the end to hold the device externally.

In some embodiments of the invention the taper part is tapered on the external side towards the end fitted to the head of the shaft and the other end to which the tubular structure will follow is broader.

In some embodiments of the invention the taper part comprises a plurality of extensions around the edges of the external side suitable to hold an attachment. In some embodiments of the invention the attachment is a patch formed from a natural dilatatory substance. In some embodiments of the invention patch is formed from *Plantago Ovata* wood.

In some embodiments of the invention the taper part has a bore in the center forming a tube, said bore having a bore size large enough to pass through the threaded and unthreaded part, and smaller than the size of the head.

In some embodiments of the invention the device is assembled from its parts as follows: (a) Fixing the taper part initially on the shaft, followed by the tubular structure and finally by the base or handle part, wherein the taper part is designed to accommodate a patch or thin layer of *Plantago ovata* wood, or (b) fixing the *Plantago ovata* cone initially on the shaft, followed by the tubular structure and finally by the base or handle part, wherein *Plantago ovata* cone is designed as a wooden cone made up of *Plantago ovata* wood.

In some embodiments of the invention the bore comprises a detection system. In some embodiments of the invention the bore comprises a flushing system. In some embodiments of the invention a diagnostic solution is used to flush the cervix, said diagnostic solution is selected from the group consisting of dilute acetic acid solution, radio contrast dye solution and saline solution. In some embodiments of the invention the bore comprises a draining system to remove biological and non-biological fluids from the cervix.

In some embodiments of the invention the device consists essentially the following parts: (a) a shaft with a head at one end and a threaded part at the other end, (b) a tubular structure as middle or connecting part covering the shaft, (c) a base or handle part, (d) a taper part to precede the middle part with provision(s) on its external surface to connect with a patch and (e) a *Plantago ovata* cone or patch.

In some embodiments of the invention provided is a synergistic combination comprising a neuro-analgesic and prostaglandins for reducing or eliminating pain and bleeding during invasive gynecological procedures. In some embodiments of the invention the neuro analgesic is Fentanyl. In some embodiments of the invention the prostaglandin is Misoprostol. In some embodiments of the invention the combination comprises Fentanyl and Misoprostol.

In some embodiments of the invention the Fentanyl in said combination is used in the range of 15 μgm to 20 μgm. In some embodiments of the invention the Misoprostol in said combination is used in the range of 75 μgm to 175 μgm.

In some embodiments of the invention the combination renders the subject painless during vaginal procedures without the use of general anesthesia. In some embodiments of the invention the combination reduces or prevents bleeding in the subject during vaginal procedures.

In some embodiments of the invention the synergistic combination further comprises an analgesic. In some embodiments of the invention the analgesic comprises one or more of Acetaminophen, Ibuprofen, Morphine, Naproxen or Oxycodone.

In some embodiments of the invention the synergistic combination further comprises an anesthetic. In some embodiments of the invention the anesthetic comprises one or more of Lidocaine, Prilocaine, Tetracaine or Iontocaine.

In some embodiments of the invention the synergistic combination further comprises a spasmolytic. In some embodiments of the invention the spasmolytic comprises one or more of Hyoscine, Carisoprodol, Cyclobenzaprine, Metaxalone, and Methocarbamol In some embodiments of the invention the synergistic combination further comprises a muscle relaxant. In some embodiments of the invention the muscle relaxant comprises one or more of thiocolchicoside, meprobamate, barbiturates, methaqualone, glutethimide, ketobemidone, and piritramide.

In some embodiments of the invention provided is a method of using the dilation device and the synergistic composition for relieving cervical blockage in a subject in need thereof comprising the steps of: (a) applying the synergistic composition to the vaginal mucosa, (b) waiting for a period of time to obtain optimal numbness in the cervical region, (c) inserting the device into the vaginal canal, and (d) waiting for a period of time to obtain optimal dilation, and thereby relieving said cervical blockage in said subject.

In some embodiments of the invention the Fentanyl is present in the range of 15 µg and the Misoprostol in the synergistic combination is present in the range of 75 to 175 µg. In some embodiments of the invention the Fentanyl is present in the range of 17 µg and the Misoprostol is present in the range of 75 to 175 µg. In some embodiments of the invention the Fentanyl is present in the range of 20 µg and the Misoprostol is present in the range of 75 to 175 µg. In some embodiments of the invention the Misoprostol in the synergistic composition is in an amount selected from the group consisting of 75 µg, 100 µg, 125 µg, 150 µg and 175 µg.

In some embodiments of the invention the Misoprostol is present in the range of 75 µg and the Fentanyl is present in the range of 15 to 20 µg in the synergistic composition. In some embodiments of the invention the Misoprostol is present in the range of 100 µg and the Fentanyl is present in the range of 15 to 20 µg. In some embodiments of the invention the Misoprostol is present in the range of 125 µg and the Fentanyl is present in the range of 15 to 20 µg. In some embodiments of the invention the Misoprostol is present in the range of 150 µg and the Fentanyl is present in the range of 15 to 20 µg. In some embodiments of the invention the Misoprostol is present in the range of 175 µg and the Fentanyl is present in the range of 15 to 20 µg in the synergistic composition. In some embodiments of the invention the Fentanyl is in an amount selected from the group consisting of 15 µg, 17 µg, and 20 µg.

In some embodiments of the invention the Fentanyl is present in the range of 15 to 20 µg and the Misoprostol is present in the range of 75 to 175 µg. In some embodiments of the invention the Misoprostol is in an amount selected from the group consisting of 75 µg, 100 µg, 125 µg, 150 µg and 175 µg and the Fentanyl is in an amount selected from the group consisting of 15 µg, 17 µg, and 20 µg.

In some embodiments of the invention the Misoprostol is present in the range of 75 µg and the Fentanyl is in an ratio of 1/5th to 1/3.75th of the concentration of said Misoprostol. In some embodiments of the invention the Misoprostol is present in the range of 100 µg and the Fentanyl is in an ratio of 1/6.65th to 1/5th of the concentration of the Misoprostol. In some embodiments of the invention the Fentanyl is present in the range of 15 µg and said Misoprostol is in range of 5× to 11.6× times the concentration of said Fentanyl.

The synergistic combination of an opioid analgesic and a prostaglandin offers a myriad of advantages over the general anesthesia procedures commonly deployed for most gynecological procedures. The usage of synergistic combination has minimal side-effects and the gynecological procedure in uterus can be performed as an outpatient procedure without the need for hospital admission or anesthesiologist.

The synergistic combination can be easily administered in an outpatient setting and starts to work in about 30-40 minutes and the effect stays for about 1-2 hours allowing the practioner to complete the procedure with ease. This is more convenient and economical that the gynecological procedures carried out with general anesthesia which often requires continuous blood pressure and heart beat monitoring. They also require the presence of anesthesiologist who has to continuously adjust the dosage to achieve optimal duration and numbness.

Synergistic combination at optimal doses not have any side effects and does not cause addiction unlike intravenous administration of Fentanyl and does not cause painful cervical contractions unlike orally administered Misoprostol. The Synergistic combination does not have dangerous side effects like irregular heart beat that are observed during intravenous Fentanyl administration. The combination is target specific to vaginal area and it produces dilatable cervix which is soft in consistency with minimal to null bleeding. It produces ideal analgesia at the cervical/vaginal region for about 60-100 minutes. This enables the practioner to carry out procedures in utero, e.g. diagnostic, removal of pathology etc. other procedures like e.g. diagnostic dilation and cuterage (D & C), polypectomy, removal of mucosal fibroids, hysterosalpingogram, hysteroscopy. All of these procedures can be performed as out-patient procedure without general anesthesia which in turn increases access to people in underserved regions because of it low cost and ease of use.

The aforesaid examples illustrate the numerous advantages involved in the usage of the synergistic composition comprising neuro-analgesic and prostaglandins, more specifically Fentanyl and Misoprostol. The synergistic composition involves small doses administered through the vaginal mucosa and is a safer therapeutic than those high doses of anesthetics administered using potent parenteral mode involving intramuscular or intravenous injections.

The synergistic compositions are specific to cervix and no contra indications to other organs have been reported. The dosage required is surprisingly in small amounts and often times a single dose is sufficient to prepare the patient for the procedure. The synergistic composition is believed to act only on the connective cervical tissue and uterus. Hence it does not have off target effects or detrimental side effects often associated with spinal tap anesthesia or general anesthesia.

The synergistic composition can be utilized for any intrauterine diagnosis and treatment. The patient trial results (Table I) indicated that over 90% of patient population tested has observed reduction of pain and bleeding during invasive gynecological procedures. The composition allows practioners to perform a variety of gynecological procedures and reproductive treatments as out-patient procedure without the need for general anesthesia or an anesthesiologist or hospital admission thereby increasing efficiency and lowering cost of treatment for patients.

In addition to lack of pain in using this combination of Fentanyl and Misoprostol, a surprising observation of lack of bleeding disturbance (no heavy bleeding from the uterus) was noticed. The synergistic combination thus provides a great advantage because it allows the practioner to see the cervical surfaces without being obscured by blood. It improves the efficiency and success rate for gynecologists performing visual intra-uterine procedures because their analysis is undeterred by bleeding in the intra-uterine environment. This in turn reduces the time required for the procedures so the operations can be performed within an hour or less as an office procedure with cost benefits to the patients.

Without being bound by theory, it is hypothesized that the lack of bleeding is due complex interactions between the cascades of events initiated by each drug. Prostaglandins such as Misoprostol activate uterine and muscle contractions which in turn initiate heavy bleeding and that generally obscures the visual and makes the procedure difficult for practioners. Cervical connective tissue dilates passively. Blood vessels and nerve filaments grow and develop in close proximity in all the tissues. Fentanyl pathway is activated through the Mu and Kappa receptors in the tissues. Fentanyl is a neuro-analgesic, but it may also act on blood vessels affecting clotting reactions thereby contributing to the "blood less" effect together with Misoprostol in an unknown molecular mechanism in these dosages by vaginal mucosal mode of delivery.

Under these diversely directed functions of A(Fentanyl)+B (Misoprostol), there seems to be an unknown but optimized and colluding extra effect in these two combined drugs. The synergistic effect seems to be observed at dosages between 75 μgm to 175 μgm of misoprostol and Fentanyl as one time dose between 15 μgm-20 μgm administered over the vaginal mucosa. This synergistic effect enables several gynecological procedures Intra Uterine Insemination (IUI) or artificial fertilization, poly cyst removal, diagnostic biopsy, Hysteroscopy such as to be performed with painfree, cervical dilation and excellent visual clarity as an office procedure with cost benefits to the patients.

BRIEF DESCRIPTION OF THE DRAWINGS

The foregoing features of embodiments will be more readily understood by reference to the following detailed description, taken with reference to the accompanying drawings, in which:

FIG. 5A depicts an embodiment in which assembled parts shaft (1), hollow cylinder or connecting part (2), and base or handle part (3) of the device are present, and FIG. 5B depicts an embodiment in which assembled parts shaft (1), hollow cylinder or connecting part (2), and base or handle part (3) and taper part (4) of the device specifically designed to accommodate dilatory part (5).

FIG. 9(a) schematically shows the folded *Plantago ovata* patch (6) for connecting with taper part (4) and FIG. 9(b) schematically shows the unfolded *Plantago ovata* patch (6).

DETAILED DESCRIPTION OF SPECIFIC EMBODIMENTS

Definitions

Figure 1:
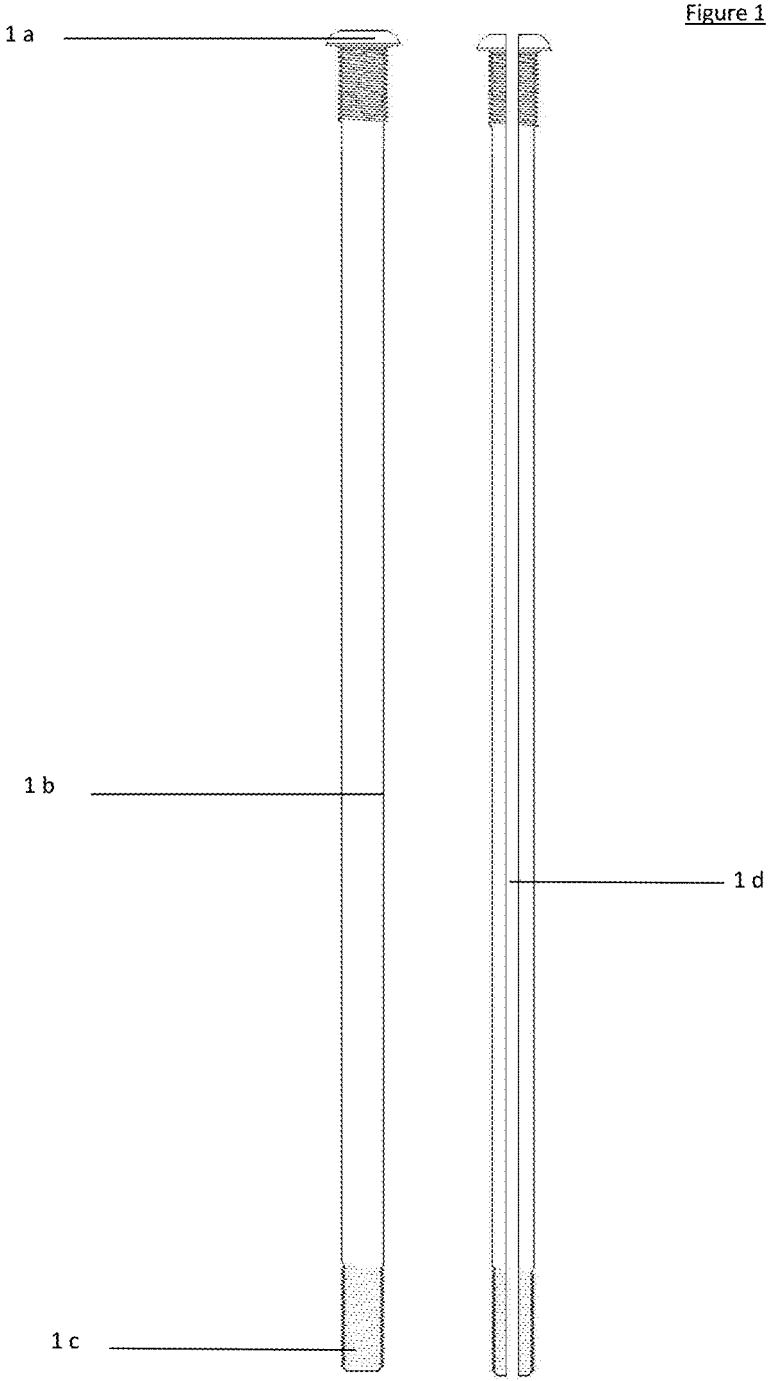
FIG. 1: schematically shows a central rod part of the device which can be termed as a shaft (1) with a head (1a) at one end and a threaded part (1c) at the other end. The part that connects (1a) with (1c) is unthreaded (1b). The shaft of the device comprises of at least one bore (1d) in the center or around the center.
Figure 2:
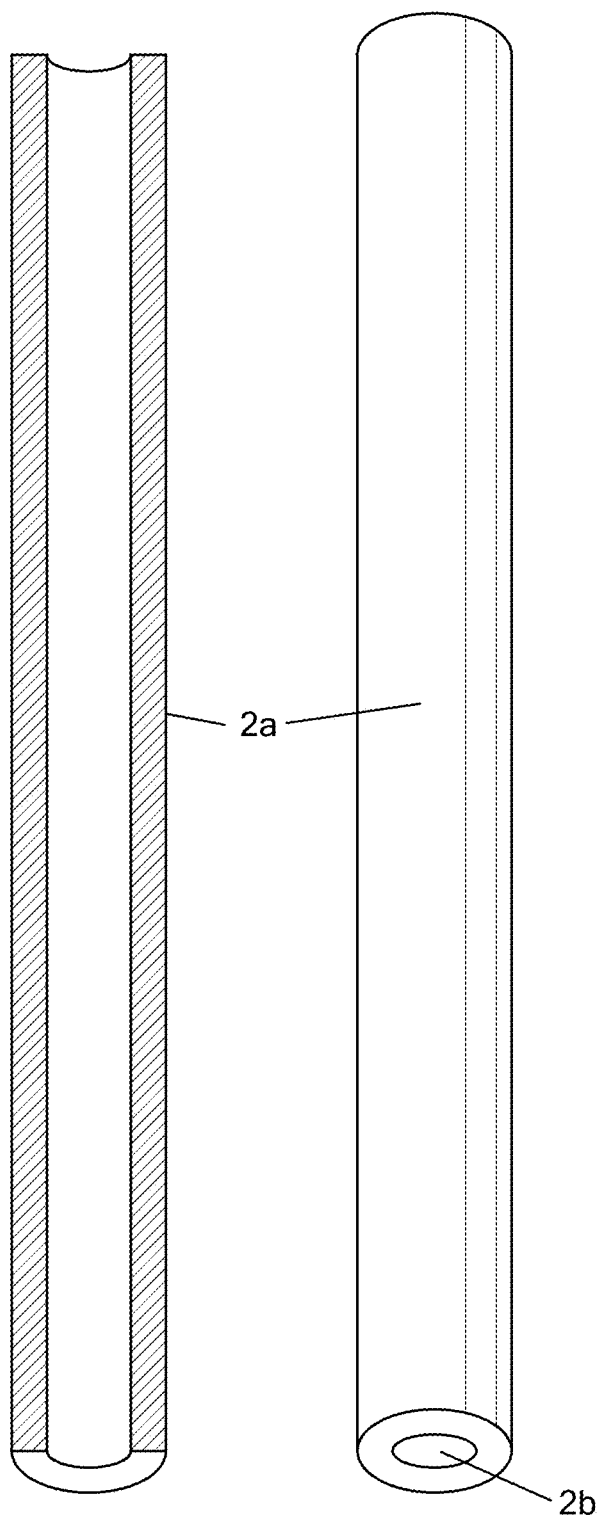
FIG. 2: schematically shows a hollow cylinder of the device with a tube-like structure (2a) with a bore (2b) sufficient to allow shaft (1) to pass through, i.e., the internal perimeter of this tube/bore is larger than the external perimeter of the shaft (1).
Figure 3:
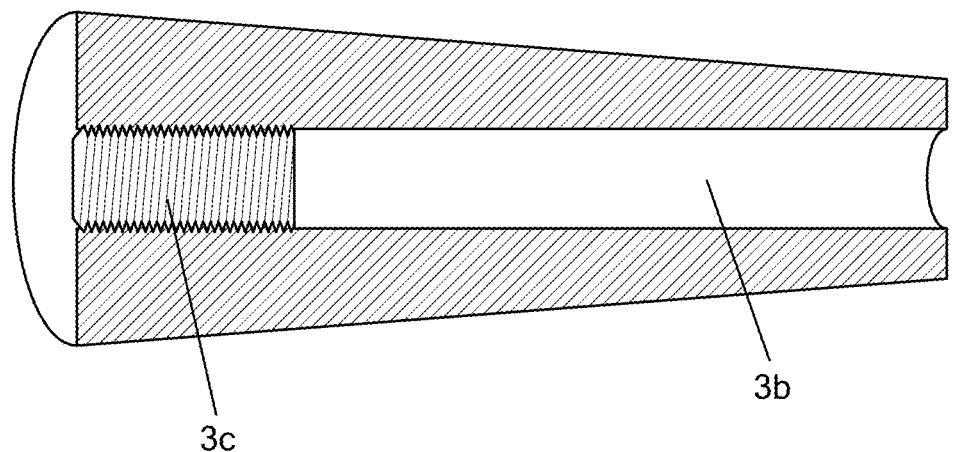
FIG. 3: schematically shows the base or handle part (3) of the device which is tubular inside with a threaded part (3c) and remaining unthreaded part (3b). The external side of this base or handle part (3) is tapered inwards, with broad portion at the end.
Figure 3:
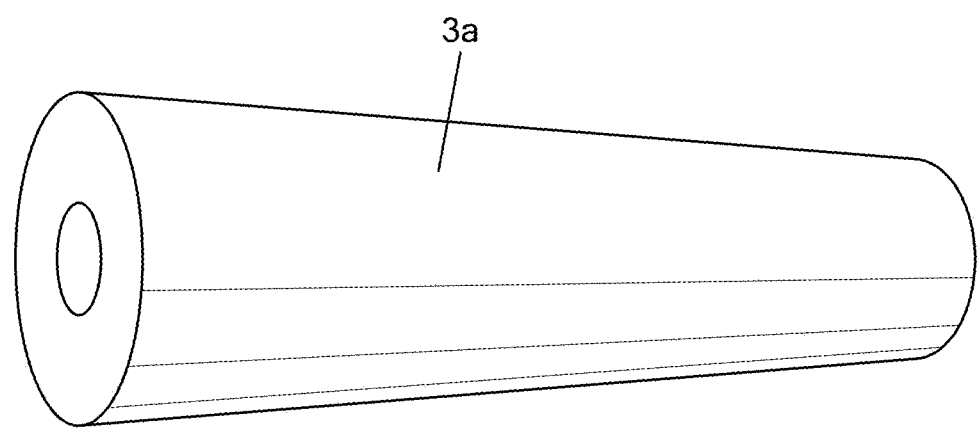
Figure 4:
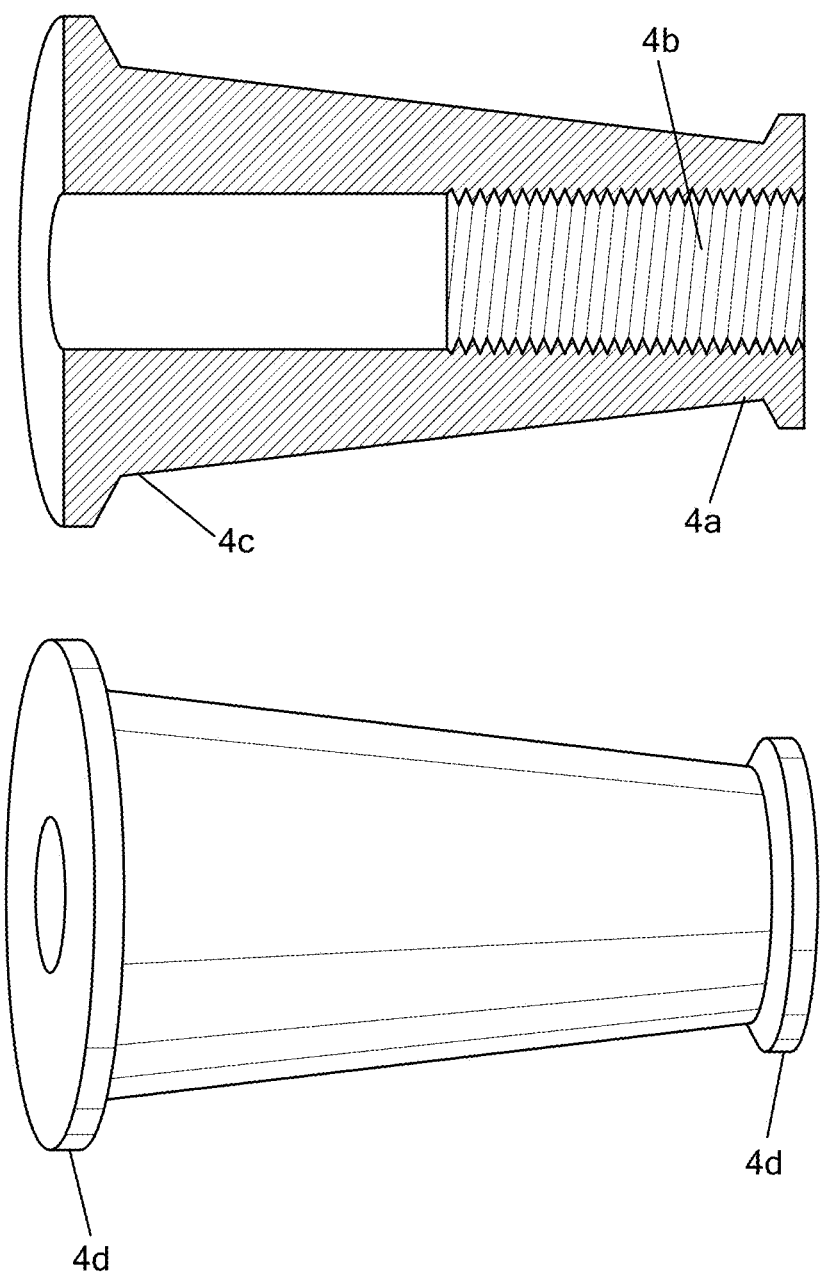
FIG. 4: schematically shows a taper part (4), which is first loaded in the shaft (1). It contains a bore (4b) in the center forming this part as a tube. This part is tapered on the external side (4a) towards the end fitted to the head of shaft (1) and the other end to which the hollow cylinder or connecting part (2) will follow is broader (4c). Taper part has a plurality of small wall like extensions (4d) around the edges of the external side (4a), in a way to hold any attachments, like patches in place.

As used in this description and the accompanying claims, the following terms shall have the meanings indicated, unless the context otherwise requires.

"Hysteroscopy" is a procedure that allows a practitioner to look inside the uterus in order to diagnose and treat causes of abnormal bleeding. Hysteroscopy is done using a hysteroscope, a thin, lighted tube that is inserted into the vagina to examine the cervix and inside of the uterus. Hysteroscopy can be either diagnostic or operative in nature.

"Hysterosalpingogram" or HSG or Hysterosalpingography or uterosalpingography, is an x-ray examination of a woman's uterus and fallopian tubes that uses a special form of x-ray called fluoroscopy and a contrast material. An x-ray (radiograph) is a noninvasive medical test that helps physicians diagnose and treat medical conditions. Imaging with x-rays involves exposing a part of the body to a small dose of ionizing radiation to produce pictures of the inside of the body. X-rays are the oldest and most frequently used form of medical imaging. Fluoroscopy is a special x-ray technique that makes it possible to see internal organs in motion. During a hysterosalpingogram, the uterus and fallopian tubes are filled with a water-soluble contrast material and the radiologist is able to use fluoroscopy to view and assess their anatomy and function.

"Intrauterine insemination" (IUT) is a fertility treatment that involves placing sperm inside a woman's uterus to facilitate fertilization. The goal of IUI is to increase the number of sperm that reach the fallopian tubes and subsequently increase the chance of fertilization.

"Cervical biopsy" is a surgical procedure in which a small amount of tissue is removed from the cervix. The cervix is the lower, narrow end of the uterus located at the end of the vagina. A cervical biopsy is usually done after an abnormality has been found during a routine pelvic exam or Pap smear. Abnormalities can include the presence of the human papillomavirus (HPV), or cells that are precancerous.

"Colposcopy" is a method of examining the cervix, vagina, and vulva with a surgical instrument called a colposcope. The procedure is usually performed if the results of pap smear are unusual. A colposcope is a large, electric microscope with a bright light that enables the practitioner to see the cervix more clearly for better diagnosis.

"Endometrial ablation" is the surgical destruction of the lining tissues of the uterus, known as the endometrium. Endometrial ablation is a treatment for abnormal bleeding of the uterus that is due to a benign (non-cancerous) condition.

"Dilation and Cuterage" or D&C is a surgical procedure in which the cervix is opened (dilated) and a thin instrument is inserted into the uterus. This instrument is used to remove tissue from the inside of the uterus (curettage). D&C is used to diagnose and treat many conditions that affect the uterus, such as abnormal bleeding. A D&C also may be done after a miscarriage.

"General Anesthesia" is a medically induced coma with loss of protective reflexes, resulting from the administration of one or more general anesthetic agents. It is carried out to allow medical procedures that would otherwise be intolerably painful for the patient; or where the nature of the procedure itself precludes the patient being awake. The optimal combination of drugs for any given patient and procedure is typically selected by an anesthetist, in consultation with the patient and the surgeon, dentist, or other practitioner performing the operative procedure. Anaesthetized patients lose protective airway reflexes (such as coughing), airway patency, and sometimes a regular breathing pattern due to the effects of anesthetics, opioids, or muscle relaxants. To maintain an open airway and regulate breathing, some form of breathing tube is inserted after the patient is unconscious. To enable mechanical ventilation, an endotracheal tube is often used, although there are alternative devices that can assist respiration, such as face masks or laryngeal mask airways.

"Cervical blockage" or cervical stenosis is a condition in which the cervix narrows or completely closes off, hindering or blocking the passage between the uterus and the vaginal canal. Cervical blockage is a potential cause of female infertility. In patients with cervical stenosis, the cervical opening is narrower than it should be and, in severe cases, may be completed closed. This can interfere with sperm getting to the egg and complicates fertility treatments like insemination or in vitro fertilization.

"Pessary" is a prosthetic device that can be inserted into the vagina to support its internal structure. It's often used in the case of urinary incontinence and a vaginal or pelvic organ prolapse. A pessary can also be used as a vessel for administering medication slowly.

"Polypectomy" is a surgical procedure used to remove polyps from the inside of the colon or uterus. Uterine polypectomy is used to remove polyps present in the endometrial tissue which are then analyzed for presence of cancerous cells.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof. Suitable pharmaceutically acceptable acid addition salts may be prepared from an inorganic acid or from an organic acid.

Illustrative embodiments of the invention provide a dilating device to clear the cervix pathway, containing an analgesic natural dilatation matter and an eluting system. It facilitates easy dilatable approach for intra-uterine procedures like, Hysteroscopy, Hysterosalpingogram, etc., In some embodiments the natural dilation matter is formed from *Plantago ovata* wood.

In another embodiment, the dilating device comprises four parts, (1) a shaft, (2) a hollow cylindrical or connecting part covering the shaft, (3) a base or handle part, and (4) a taper part to precede the hollow cylindrical part with provision(s) on its external surface to connect with a patch.

In another embodiment, the central part of the gynecological or dilating device is referred to as a shaft (1) with a head (1a) at one end and a threaded part (1c) at the other end. The part that is in between (1a) and (1c) is unthreaded (1b). The shaft part (1) of the device comprises of at least one bore (1d) in the center or around the center. In addition to this minimum of one bore, it can have additional bores to accommodate more functions like, fluid transmission, light sources, camera connectivity, probes or surgery related equipment and also have an optional separate drain provision to remove any undesired liquid, during the gynecological procedure.

In an illustrative embodiment of the invention, the central unthreaded part of the shaft (1) is covered by a tubular structure, to connect the taper part (4) and base or handle part (3) of the device. The tubular structure has a smooth external surface (2a) and is provided with a horizontal bore (2b) sufficient enough to allow the shaft part (1) to pass through, i.e., the internal perimeter of this tube/bore (2b) is larger than the external perimeter of the shaft part (1).

In an illustrative embodiment of the invention, the base or handle part (3) for the shaft (1), is tubular inside with a part threaded (3c) and remaining unthreaded (3b). The external side of this base or handle part (3) is tapered inwards towards the head (1a) of the shaft (1), with wider portion at the end to hold the device externally. The internal threaded portion (3c) of this base part (3) will connect with the threaded (1c) of the shaft (1). The connection is similar to a bolt and nut mechanism, sufficient to hold the parts 4, 2 and 3 of the device in seriatim, with the shaft.

In an illustrative embodiment of the invention, the first part to be loaded in the shaft (1) is the taper part (4). The taper part is tapered on the external side (4a) towards the end fitted to the head (1a) of shaft (1) and the other end to which the hollow cylindrical or connecting part (2) will follow is broader (4c). The taper part has a small wall like extensions (4d) around the edges of the external side (4a), in a way to hold any attachments, like patches in place. The taper part (4), also has a bore (4b) in the center forming this part as a tube, having a bore size large enough to pass through the unthreaded part (1b) and threaded (1c), but smaller than the size of the head (1a) of the shaft (1). The bore (4b) has grooves/threads as a part of the bore, but in contrast to the base or handle part (3) at the tapered side. The threads will enable the taper part (4), to fix itself with head (1a) of the shaft (1).

Figure 5:
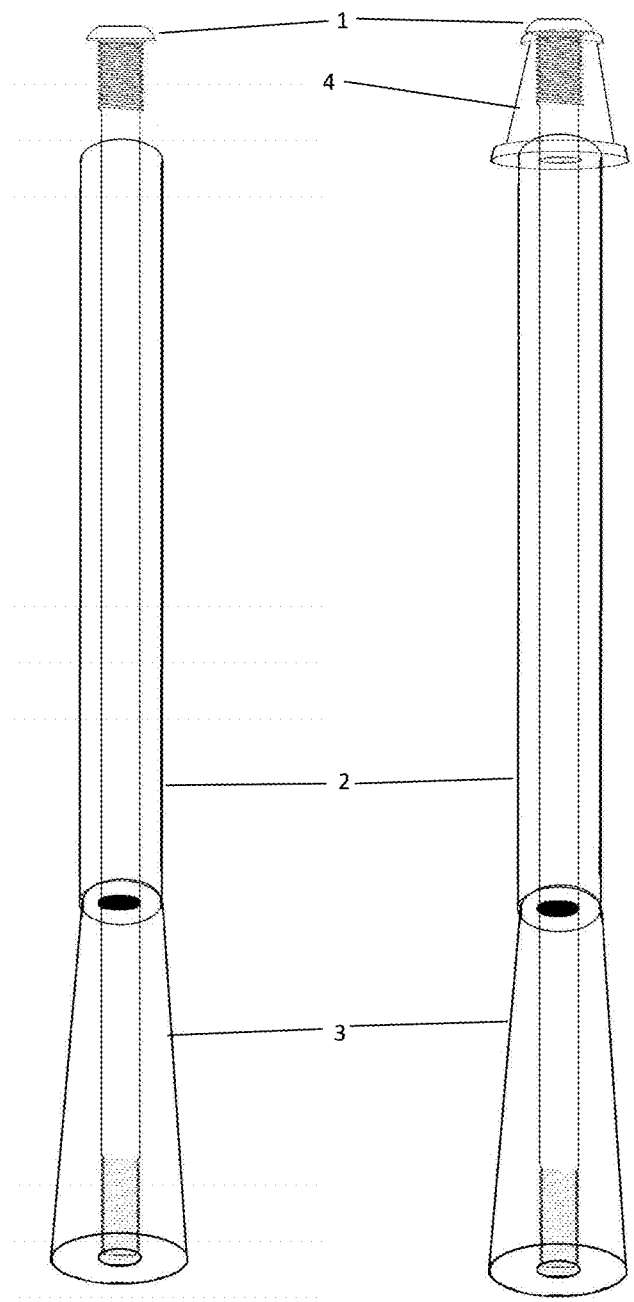
FIG. 5: schematically shows the device in accordance with the illustrative embodiments of the invention.

In some embodiments the various parts (1-4) upon assembly provide the assembled device as schematically shown in FIG. 5. In another embodiment, the head part (1a) is not followed by taper part (4), but rather by a substantially similar shaped wooden piece referred to as dilatory part (5) to serve the purpose. The FIG. 5A depicts this embodiment wherein assembled parts 1, 2, and 3 of the device to accommodate specifically designed dilatory part (5).

FIG. 5B schematically shows another embodiment in which the taper part (4) is designed to accommodate a patch (6) or thin layer of *Plantago ovata* wood to serve as natural dilatation matter. The taper part (4) with the wooden patch (6) assembled to it, in toto will mimic the shape of dilatory part (5) which is also formed from natural dilatation matter such as *Plantago ovata* wood.

Figure 6:
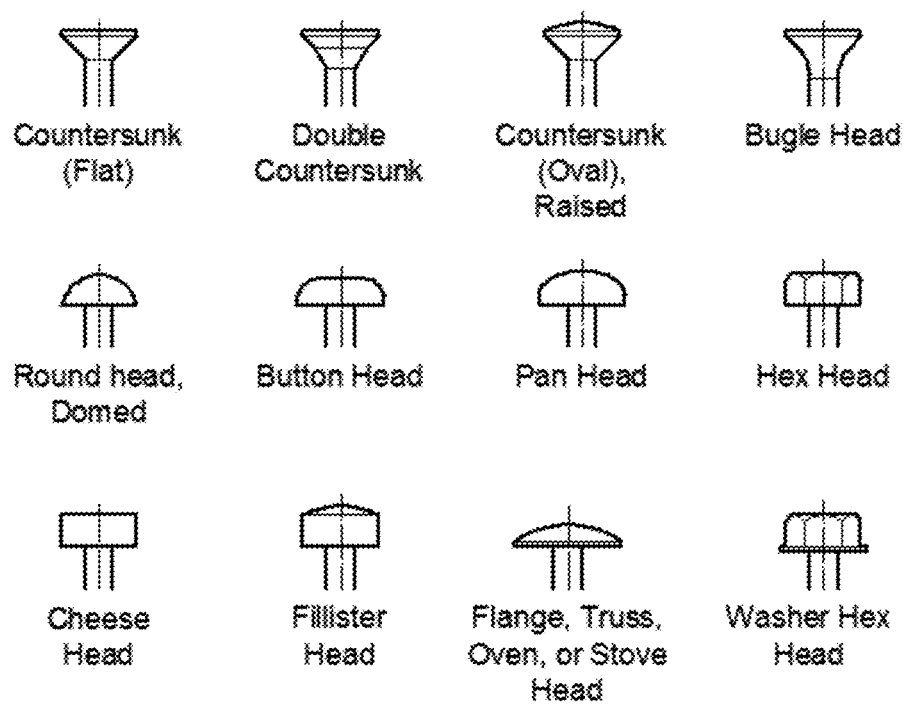
FIG. 6: schematically shows the shape of several embodiments of head part (1a) of the shaft (1).
Figure 7:
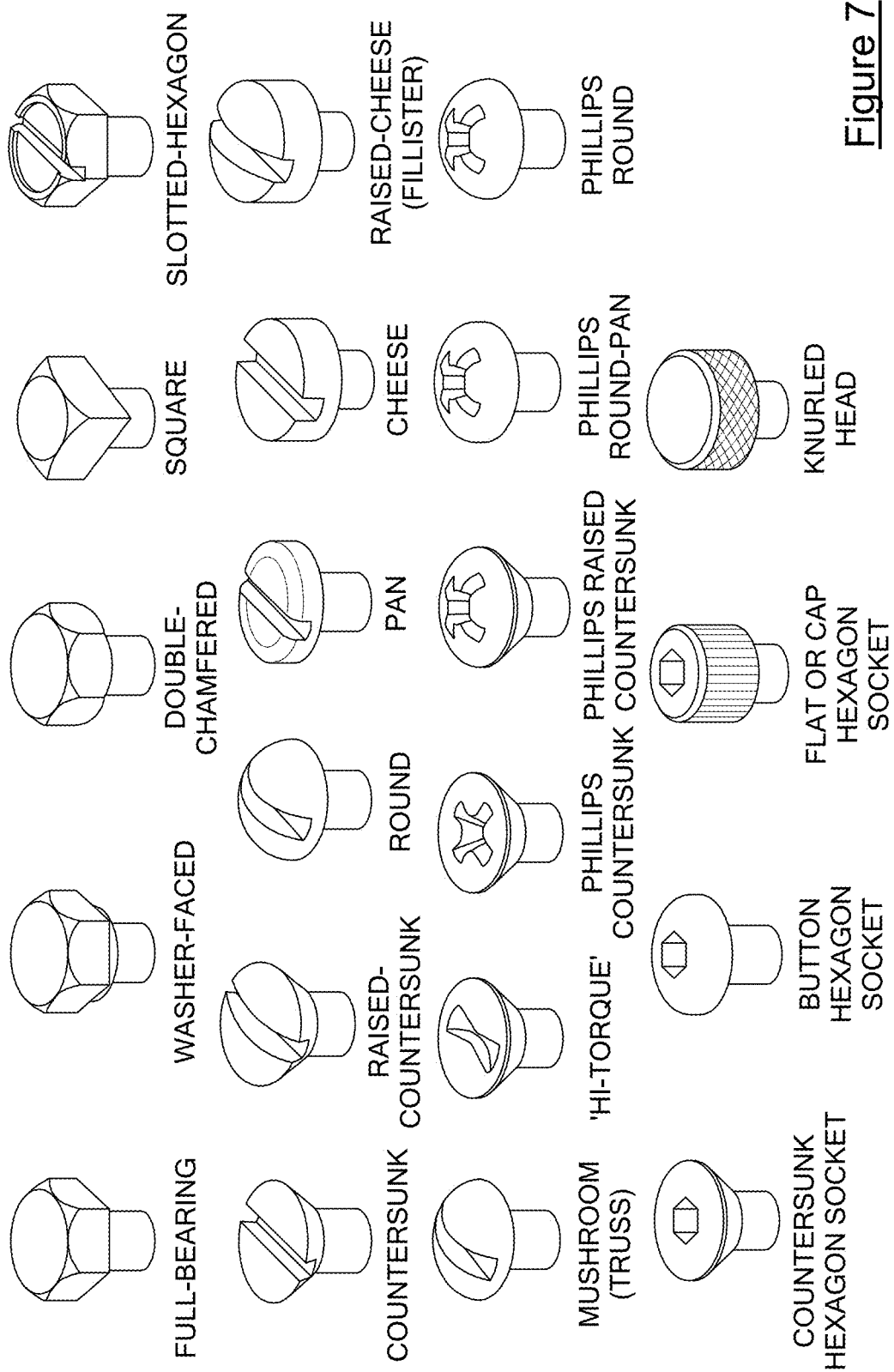
FIG. 7: schematically shows the shape of several embodiments of head part (1a) of the shaft (1) from top, which has provisions to tighten/connect it with its attachments and threaded with part 3c. These provisions also have a central bore to be in line with the bores of other parts like 1d, 4b.
Figure 8:
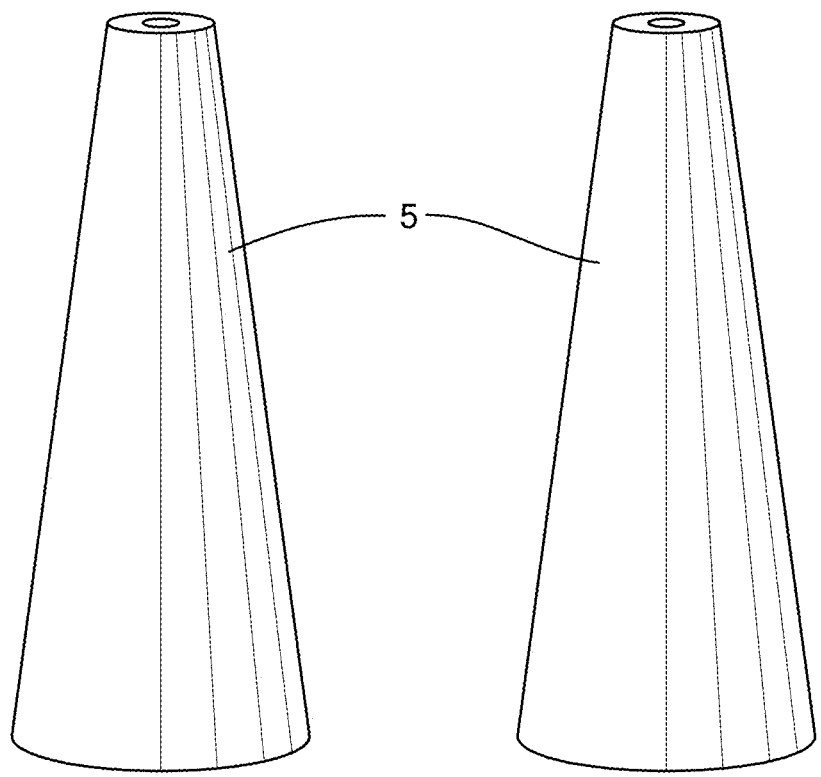
FIG. 8: schematically shows the dilatory part (5) of the device formed from *Plantago ovata* wood in accordance with illustrative embodiments of the invention.

In some embodiments of the invention, the head (1a) of the shaft (1) of the device can have any of the shapes schematically depicted in FIGS. 6 and 7, having provisions to tighten/connect it with its attachments via inbuilt threads. These provisions also have a central bore to be in line with the bores of other parts like 1d, and 4b.

In some embodiments of the invention the front end of the device, the wooden cone or dilatory part (5) or the patch formed from natural dilatator matter (6) is made up of a *Plantago ovata* wood.

In another embodiment of the invention the central bore or hole in the device is designed to accommodate various probes, light source, drainage/suction tubes and to accommodate any other procedure related devices.

In some embodiments the dilation device can be used for cervical diagnosis by placing optimal detection systems inside one or more of bores present in the device to detect changes in the physiology of the cervical/vaginal region.

In some embodiments the detection system can be a fiber optical camera that can image the interior of cervix in real time.

In another embodiment the detection system can be endomicroscopic probes that can visualize cell activity. (See *Nonlinear optical endomicroscopy for label-free functional histology in vivo*, Wenxuan Liang et al., Light: Science & Applications volume 6, page e17082 (2017)).

In another embodiment the dilation device can be used to collect cervical lavage by having a flushing system in one bore and a draining system in another bore located in the central part of the shaft. The flushing system allows the practioner to pump saline solution into the cervix and the draining system allows the practioner to collect the lavage that contains sample from the cervix/vagina. The solution or fluid being drained can be both biological and non-biological fluids. The cervical lavage thus collected from the drainage system in the bore can be analyzed for the presence of pathogenic DNA or abnormalities for detection purposes.

In another embodiment the dilation device can be used to irrigate cervix with radio contrast solution by a flushing system present in one bore of the device and the solution can be drained by using the draining system present in another bore of the device. The treated surface of the cervix can be visualized by using optical or fluorescent probes located in another bore of the device.

In another embodiment the dilation device can be used to irrigate cervix with low concentration of acetic acid by a flushing system present in one bore of the device and the acetic acid solution can be drained by using the draining system present in another bore of the device. The treated surface of the cervix can be visualized by using optical probes located in another bore of the device to detect the presence of human papilloma virus infections which appear as white lesions on the surface.

In some embodiments the device is made up of one or more rigid or flexible or semi flexible materials like surgical grade steel, silicon, plastic or with tempered glass. It can also be made with materials that are reusable after sterilization or with materials that can be used only once. The procedure of using the gynecological or dilation device illustrated by the non-limiting examples 1-3.

In another embodiment of the invention, provided is a synergistic combination comprising a neuro-analgesic and a prostaglandin for application in vaginal mucosal area to reduce pain and bleeding during uterine procedures.

In another embodiment of the invention, provided is a synergistic combination comprising Fentanyl and Misoprostol for application in vaginal mucosal area to reduce pain and bleeding during uterine procedures.

In another embodiment the synergistic combination may be in the form of a gel or pessary that is applied on the vaginal mucosal once or twice for a few hours (3-4 hours) prior to any uterine procedure in order to reduce pain and bleeding during the uterine procedure.

In general, the medical procedures in gynecology such as Intra Uterine Insemination (IUI) or artificial fertilization, artificial abortion, poly cyst removal, diagnostic biopsy, Hysteroscopy etc. require the use of general anesthesia. The process of sedating and reviving patients for aforesaid procedures is very complex and requires the presence of a specialist such as anesthesiologist for administering and maintaining the anesthesia level during the procedure. The patient needs to be hospitalized and will continue to be in the unconscious state for extended period of time even after the completion of the gynecological procedure.

The drug combinations known and practiced conventionally by the physicians in the prior art are either for increasing the anesthetic effect, or for inducing numbness, during artificial abortion or vaginal medical procedure. A synergistic composition that renders the complicated vaginal procedure involving the administration of general anesthesia into a simple procedure such as an out-patient procedure which is painless with little or no bleeding and is also cost effective to the patients is needed. The inventors have recognized the need and have provided synergistic compositions that eliminate the need for general anesthesia and offer the ability to practioners to perform gynecological procedures without pain or bleeding at an economical price point for the patients without the need for hospital admissions or the presence of anesthesiologist.

General anesthesia is often invasive requiring intravenous injections or spinal taps which puts the patients at risk for various side effects and complications. The general anesthesia dosage is calculated based on the weight of the patient and the duration of the procedure. Often time mistakes are made in the dosage leading to prolonged sedation which can result in sudden drop in blood pressure and or hear beats. Improper general anesthesia can also result in premature awakening during the procedure which can cause severe discomfort. In some embodiments of the invention provided are synergistic compositions that are safe and efficacious and don't have the risks associated with general anesthesia owing to their smaller dosages and target specific due to their application through vaginal mucosal route.

In some embodiments of the invention provided are synergistic compositions to evade anesthetized vaginal procedures, comprising a neuro-analgesic and prostaglandins for performing painless and reduced or nil bleed gynecological procedures.

Another embodiment of the invention provides a synergistic combination, wherein said neuro analgesic is Fentanyl.

Another embodiment of the invention provides a synergistic combination, wherein said prostaglandin is Misoprostol.

In some embodiments of the invention, Fentanyl is used in the range of 15 µgm-20 µgm.

In some embodiments of the invention, Fentanyl is used in the range of 2 µg, 4 µg, 6 µg, 8 µg, 10 µg, 12 µg, 14 µg, 16 µg, 18 µg and 20 µg.

In some embodiments of the invention, Fentanyl is used in the range of 3 µg, 6 µg, 9 µg, 12 µg, 15 µg, 18 µg, 19 µg, and 20 µg.

In another embodiment of the invention, Misoprostol is used in the range of in the range of 75 µgm to 175 µgm/kg.

In some embodiments of the invention, Misoprostol is used in the range of 75 µg, 80 µg, 85 µg, 90 µg, 95 µg, 100 µg, 105 µg, 110 µg, 115 µg, 120 µg, 125 µg, 130 µg, 135 µg, 140 µg, 145 µg, 150 µg, 155 µg, 160 µg, 165 µg, 170 µg and 175 µg.

In some embodiments of the invention, Misoprostol is used in the range of 75 µg, 78 µg, 82 µg, 86 µg, 90 µg, 94 µg, 98 µg, 102 µg, 106 µg, 110 µg, 114 µg, 118 µg, 122 µg, 126 µg, 130 µg, 134 µg, 138 µg, 142 µg, 146 µg, 150 µg, 154 µg, 158 µg, 162 µg, 166 µg, 170 µg, and 174 µg Another embodiment of the invention provides a synergistic combination that renders the subject painless upon administration during gynecological or reproductive procedures.

Another embodiment of the invention provides a synergistic combination that reduces or prevents bleeding upon administration during gynecological or reproductive procedures.

In some embodiments of the invention, the synergistic composition comprises Fentanyl also known as Fentanyl, an opioid analgesic (Formula: C22H28N2O) and Misoprostol (a prostaglandin, a cervical dilator having Formula: C22H38O5)

In some embodiments of the invention, the synergistic composition is administered with a dose of 100 µgm to 150 µgm of Misoprostol and Fentanyl dose being 9%-15% of the parenteral dose in this combination.

In another embodiment, the synergistic composition further comprises suitable additive to make a jelly or pessary that can be inserted over the vaginal posterior fornix.

In some embodiments, the synergistic composition is administered once.

In another embodiment, the synergistic composition is administered more than once before the commencement of the gynecological procedure.

In some embodiments of the invention provided is a synergistic combination comprising Fentanyl, Misoprostol and optionally an analgesic such as Acetaminophen, Ibuprofen, Morphine, Naproxen or Oxycodone.

In some embodiments of the invention provided is a synergistic combination comprising Fentanyl, Misoprostol and optionally an anesthetic such as Lidocaine, Prilocaine, Tetracaine or Iontocaine.

In some embodiments of the invention provided is a synergistic combination comprising Fentanyl, Misoprostol and optionally a spasmolytic such as hyoscine, carisoprodol, cyclobenzaprine, metaxalone, and methocarbamol.

In some embodiments of the invention the synergistic combination comprises Fentanyl, Misoprostol and optionally a muscle relaxant such as thiocolchicoside, meprobamate, barbiturates, methaqualone, glutethimide, ketobemidone, and piritramide.

In some embodiments of the invention the synergistic combination comprises Fentanyl, Misoprostol and optionally a neuroanalgesic.

In some embodiments of the invention provided is a method of using the dilatory device and the synergistic composition in invasive gynecological procedures. The synergistic composition comprising Fentanyl (15-20µg) and Misoprostol (75-175µg) is applied to the vaginal mucosa. After 40-60 minutes past administration of the composition optimal numbness in the cervical/vaginal region is achieved. After achieving optimal numbness, the dilatory device is assembled as described elsewhere in the specification and is then inserted into the vaginal canal. The device can be left in position for 3-4 hours. Optionally the *Plantago ovata* cone or *Plantago ovata* patch rolled in the form of cone over the taper part can be left in position inside the vaginal canal and the shaft along with the rest of the device can be removed. This would facilitate easy movement and comfort for the subject while she waits for the cervical blockage to be cleared. After clearance of cervical blockage is achieved the cone or patch is removed and discarded.

Various embodiments of the present invention may be characterized by the potential claims listed in the paragraphs following this paragraph (and before the actual claims provided at the end of this application). These potential claims form a part of the written description of this application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public.

The embodiments of the invention described above are intended to be merely exemplary; numerous variations and modifications will be apparent to those skilled in the art. All such variations and modifications are intended to be within the scope of the present invention as defined in any appended claims.

Pharmaceutical Excipients and Formulations

The pharmaceutical composition can contain formulation agent(s) for modifying, maintaining, or preserving, for example, the pH, osmolarity, viscosity, clarity, color, isotonicity, odor, sterility, stability, rate of dissolution or release, adsorption, or penetration of the composition. Suitable formulation agents include, but are not limited to, amino acids (such as glycine, glutamine, asparagine, arginine, or lysine), antimicrobials, antioxidants (such as ascorbic acid, sodium sulfite, methionine or sodium hydrogensulfite), buffers (such as borate, bicarbonate, Tris-HCl, histidine, citrates, phosphates, or other organic acids), bulking agents (such as manitol or glycine), chelating agents (such as ethylenediamine tetraacetic acid (EDTA)), complexing agents (such as caffeine, polyvinylpyrrolidone, betacyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or manitol sorbitol), delivery vehicles, diluents, excipients and/or pharmaceutical adjuvants (see, e.g., Remington's Pharmaceutical Sciences (18th Ed., A. R. Gennaro, ed., Mack Publishing Company 1990), and subsequent editions of the same, incorporated herein by reference for any purpose).

The primary vehicle or carrier in a pharmaceutical composition can be either aqueous or non-aqueous in nature. For example, a suitable vehicle or carrier for administration can be water, physiological saline solution, or artificial cerebrospinal fluid, possibly supplemented with other materials common in compositions for mucosal administration. Neutral buffered saline or saline mixed with serum albumin are further exemplary vehicles. Other exemplary pharmaceutical compositions comprise Histidine or Tris buffer of about pH 6.0-8.5, which can further include sorbitol or a suitable substitute.

Additional pharmaceutical compositions will be evident to those skilled in the art, including formulations involving Fentanyl and Misoprostol, in sustained- or controlled-delivery formulations. Techniques for formulating a variety of other sustained- or controlled-delivery means, such as liposome carriers, bio-erodible microparticles or porous beads and depot injections, are also known to those skilled in the art (see, e.g., International Publication No. WO93/15722, which describes the controlled release of porous polymeric microparticles for the delivery of pharmaceutical compositions, and Wischke & Schwendeman, 2008, Int. J. Pharm. 364: 298-327, and Freiberg & Zhu, 2004, Int. J. Pharm. 282: 1-18, which discuss microsphere/microparticle preparation and use). As described herein, a hydrogel is an example of a sustained- or controlled-delivery formulation.

Additional examples of sustained-release preparations include semipermeable polymer matrices in the form of shaped articles, e.g. films, or microcapsules. Sustained release matrices can include polyesters, hydrogels, polylactides (U.S. Pat. No. 3,773,919 and European Patent No. 0058 481), copolymers of L-glutamic acid and gamma ethyl-L-glutamate (Sidman et ah, 1983, Biopolymers 22: 547-56), poly(2-hydroxyethyl-methacrylate) (Langer et ah, 1981, J. Biomed. Mater. Res. 15: 167-277 and Langer, 1982, Chem. Tech. 12: 98-105), ethylene vinyl acetate (Langer et al, supra) orpoly-D(-)-3-hydroxybutyric acid (European Patent No. 0 133 988). Sustained-release compositions can also include liposomes, which can be prepared by any of several methods known in the art. See, e.g., Epstein et al, 1985, Proc. Natl. Acad. Sci. U.S.A. 82: 3688-92; and European Patent Nos. 0 036 676, 0 088 046, and 0 143 949.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

Administration

The composition can be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration. In order to deliver the synergistic combination of Fentanyl and Misoprostol as disclosed herein, at a predetermined rate such that the drug concentration can be maintained at a desired therapeutically effective level over an extended period, a variety of different approaches can be employed.

In one example, a hydrogel comprising a polymer such as a gelatin (e.g., bovine gelatin, human gelatin, or gelatin from another source) or a naturally-occurring or a synthetically generated polymer can be employed. Any percentage of polymer (e.g., gelatin) can be employed in a hydrogel, such as 5, 10, 15 or 20%. The selection of an appropriate concentration can depend on a variety of factors, such as the therapeutic profile desired and the pharmacokinetic profile of the therapeutic molecule.

Examples of polymers that can be incorporated into a hydrogel include polyethylene glycol ("PEG"), polyethylene oxide, polyethylene oxide-co-polypropylene oxide, co-polyethylene oxide block or random copolymers, polyvinyl alcohol, poly(vinyl pyrrolidinone), poly(amino acids), dextran, heparin, polysaccharides, polyethers and the like.

Another factor that can be considered when generating a hydrogel formulation is the degree of crosslinking in the hydrogel and the crosslinking agent. In some embodiments, cross-linking can be achieved via a methacrylation reaction involving methacrylic anhydride. In some situations, a high degree of cross-linking may be desirable while in other situations a lower degree of crosslinking is preferred. In some cases a higher degree of crosslinking provides a longer sustained release. A higher degree of crosslinking may provide a firmer hydrogel and a longer period over which drug is delivered. Any ratio of polymer to crosslinking agent (e.g., methacrylic anhydride) can be employed to generate a hydrogel with desired properties. For example, the ratio of polymer to crosslinker can be, e.g., 8:1, 16:1, 24:1, or 32:1. For example, when the hydrogel polymer is gelatin and the crosslinker is methacrylate, ratios of 8:1, 16:1, 24:1, or 32:1 methyacrylic anhydride:gelatin can be employed.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction and preparation conditions, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

Example 1: Assembling the Device with Dilatory Part (5)

The shaft (1) of the device is taken, to which the dilatory part (5) is added. The dilatory part is the wooden cone and the thread in this cone will ensure the proper fixation of the cone (5) with the shaft (1) near the head (1a). The dilatory part (5) is followed by hollow cylinder or connecting part (2) and then by the base or handle part (3). The base or handle part (3) has threads at the rear end and ensures proper assembling of the rest of the parts in place over shaft (1). Once the parts 1, 5, 2 and 3 are assembled, the device can be used for performing desired gynecological procedures.

Example 2: Assembling the Device with Taper Part (4) and Patch (6)

Figure 9:
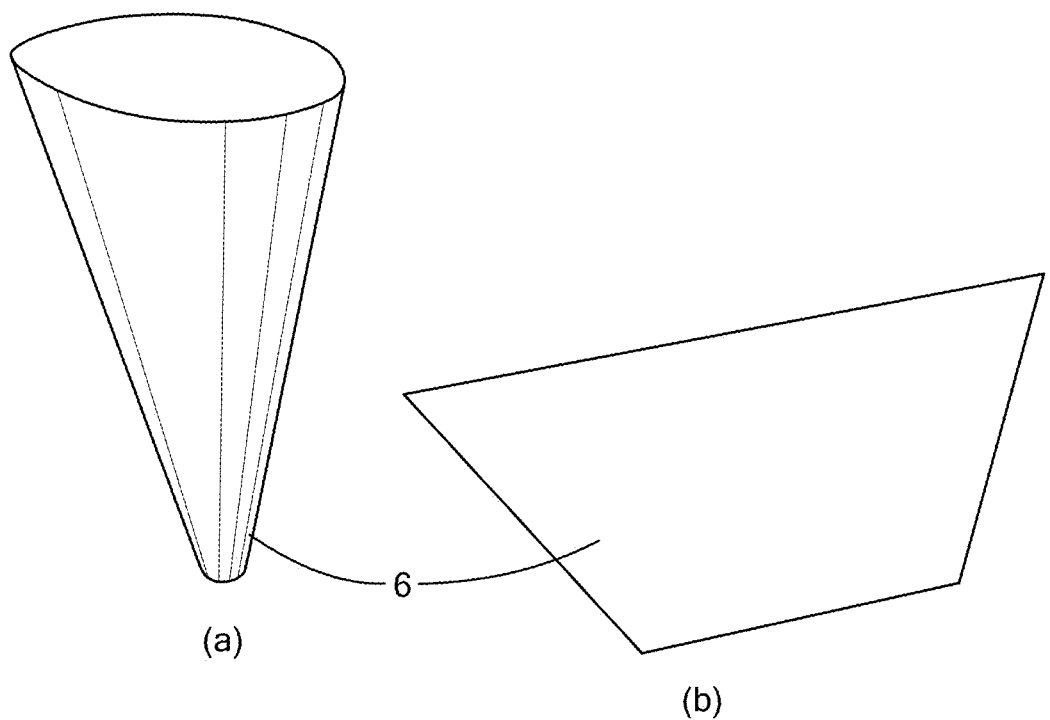
FIG. 9.
Figure 10:
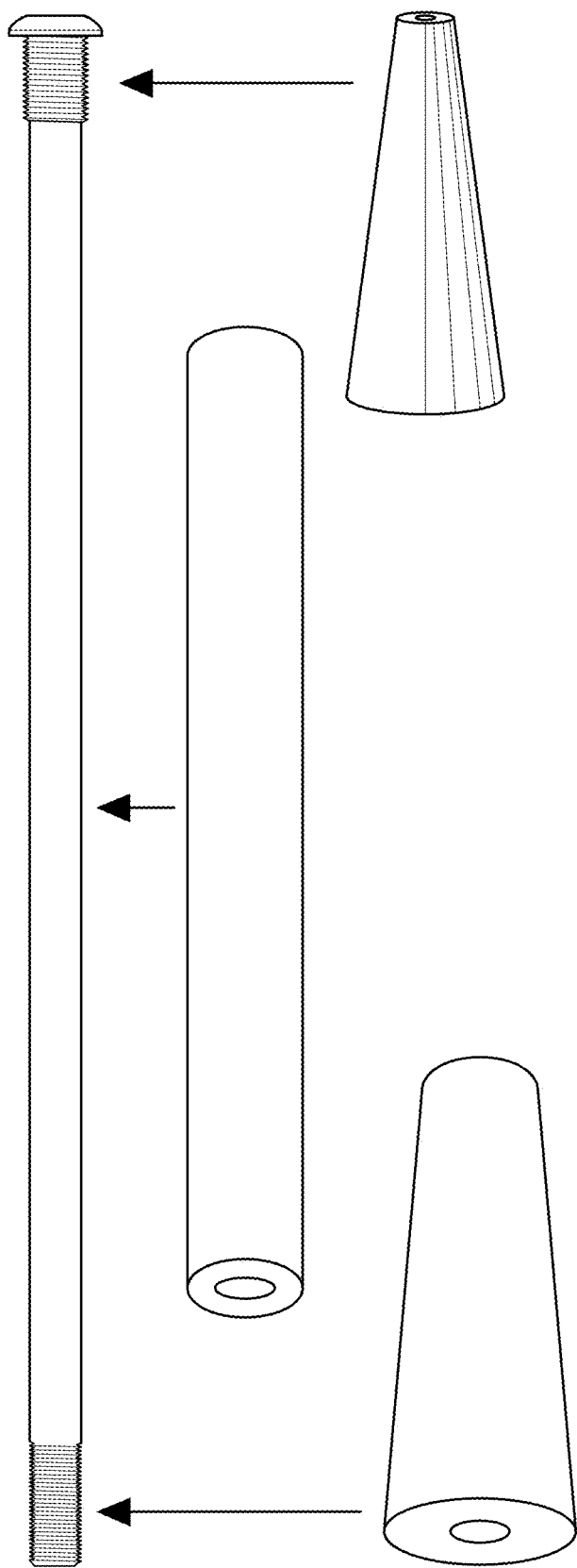
FIG. 10: schematically shows the exploded view of the gynecological device in accordance with the illustrative embodiments of the invention.
Figure 11:
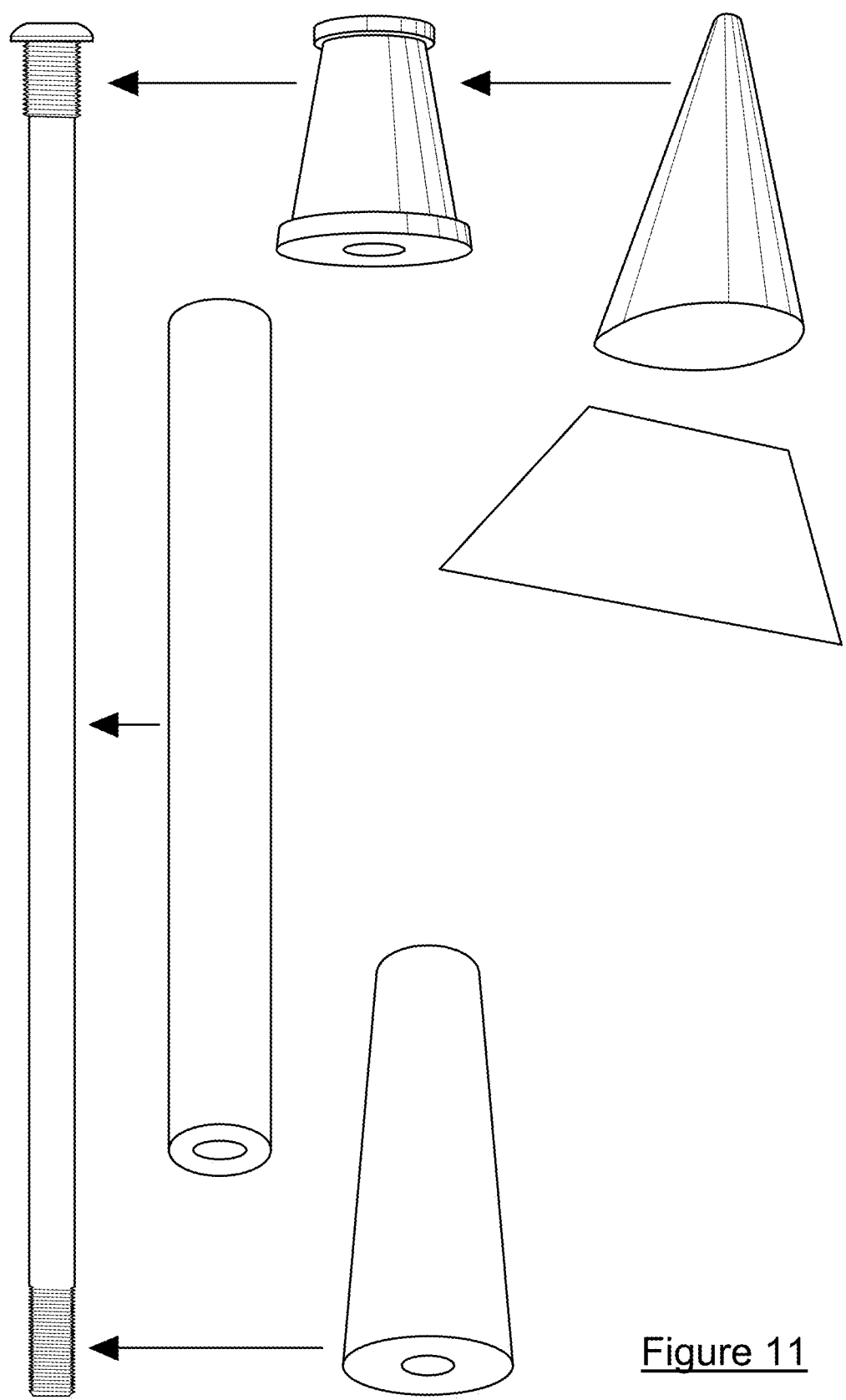
FIG. 11: schematically shows the exploded view of the gynecological device with patch (6) formed from *Plantago ovata* wood in accordance with the illustrative embodiments of the invention.

The shaft part (1) of the device is taken, to which the taper part (4) is added. The taper part (4) is provided with a provision to accommodate a patch (6) and to connect internally by a threaded means to attach firmly with the head (1a) of the shaft (1). The wooden patch (6) can be bent to form a cone (as shown in FIG. 9) to cover the surface of the taper part (4). This combination of taper part (4) with patch (6) followed by hollow cylinder or connecting part (2) and base or handle part (3) completes the assembly of the device. The base or handle part has threads at the rear end and ensures proper assembling of the earlier parts in place over shaft (1). Once the parts 1, 4, 6, 2 and 3 are assembled the device, can be used for performing desired gynecological procedures.

Example 3: Application of the Device in Gynecological Procedures

After assembling of the parts as per any of the earlier examples, the device is appropriately placed in the cervix of the subject and allowed to expand for a period of three to four hours, or as required by the practicing physician. Once the cervix part is dilated to the desired level, the device can be removed with ease and can be re-used after sterilization by replacing the *Plantago ovata* part, subject to the nature of the device material.

Once the cervix dilation is achieved, any required procedure can be carried out through the central pore of the device, if surgical procedures needed to be performed, can be completed through the pore, and with the help of the sophisticated probes meant for such purposes. If any water gets accumulated during any of the procedure, they can be drained through the pore. Customarily, the dilation of the cervix is not practiced as an out-patient procedure and such procedures involve an active assistance of an anesthetist. The device allows practioners to perform cervix dilation without the need for general anesthesia as on outpatient procedure.

In an illustrative embodiment of the invention, the device is inserted into cervix without any anesthesia and the cervix dilation is achieved without any pain to the subject. At the end of dilation, the device is removed from the cervix. During the dilation procedure, if the patient wishes to move around, it is possible for the subject to move without any pain.

The dilation device thus offers several benefits and serves to enable treatment of cervical blockage as an outpatient procedure without the need for general anesthesia. Since an anesthesiologist is not required for the procedure to be conducted, it allows hospitals and practioners to save time reduce costs which in turn makes the procedure economically viable to the patients.

The dilation device can optionally contain an elution system. The eluting system would have an outer layer of dilation with a central eluting system for drug delivery and a fine metallic piece of retrieval of the system. The dimensions of the system would vary between 2 cm in length with an outer diameter of 2 to 4 mm interspersed with micro channels for drug elution.

The dilation device can also be employed for IVF-embryo transfer procedure in cervical "blockage" to open up the pathway for easy embryo transfer.

Example 4: Dosage Analysis for Synergistic Composition

Fentanyl is given parentally as an intravenous injection for pain and times with breathing difficulties in patients. Misoprostol is a cervical primer that causes heavy bleeds on overdose and is commonly used for inducing abortion. These drugs are used always in combination with other drugs like Propofol or with Diclofenac or Ibuprofen to achieve desired results. In addition, the mode of administration of fentanyl is either parental or through intravenous injection. The drug combination needs to be carefully enumerated, as Fentanyl is given generally for pain relief and at times for breathing difficulties in patients. Fentanyl is a powerful drug and at improper dosages can cause lethal side effects like cardiac arrest and can also result in narcotic addiction. Fentanyl is administered to patients with chronic pain who no longer respond to conventional opiate drugs. Misoprostol is used for inducing abortion and at high doses can cause severe cervical contractions. Generally Fentanyl and Misoprostol are not administered in combination owing to the risk of severe side effects associated with each of them.

In the quest to determine a suitable composition that would enable gynecological procedures to be conducted without bleeding or pain and without the need of general anesthesia, inventors tested several combinations of drugs and determined surprisingly that the combination of Fentanyl and Misoprostol synergistically produced dilation coupled with numbness when administered to the vaginal mucosa which then allows gynecological procedures to be conducted without pain or bleeding even without general anesthesia .Misoprostol; is commercially available in the form of tablets and was used for preparing the composition for trial studies. Fentanyl solution is commercially available as TAL-GESIL (CCM Duopharma Biotech) and was used for preparing the composition along with Misoprostol. Therapeutic dosage was determined by varying the amounts of Fentanyl and Misoprostol. The results of the dosage study are described in detail in Example 7. At the optimized dosage ranges, the combination surprisingly had no side effects like addictive tendencies or irregular heartbeats and it produced the desired results of smooth dilation with localized numbness within the desired time that allows gynecological procedures to be carried out on patients without pain or bleeding.

Example 5: Animal Studies

Animal studies were carried out first to test the efficacy of the synergistic composition of Fentanyl and Misoprostol prior to testing on patients. Two rabbits were used for animal trials. Misoprostol was used at a dosage of 10 µg/kg and Fentanyl was used at a dosage of 50 µg/kg. The synergistic composition was made into a vaginal sachet form by combining the administration of Misoprostol and Fentanyl. The vaginal sachet containing Misoprostol was then inserted to the vaginal cloaca area of the rabbits at the same time Fentanyl solution was instilled in the vagina. After 45 minutes past administration, the efficacy of the combination was analyzed by observing the pain threshold and cloacal dilation of the rabbits.

Pain:

—No pain was noted when cloacal opening is examined by using instruments and both animals were conscious with no resistance. Pain scored observation was found to be satisfactory for each dosed animal. This result was observed after 45 minutes of drug therapy.

Cloacal Dilation:

The cloacal opening was dilated using tiny dilators designed for small mammals and surprisingly no resistance was observed from the rabbits indicating lack of pain and smooth dilation was achieved which enabled complete examination of the cervical region of the rabbits with ease.

Example 6—Dose Determination for Vaginal Mucosa Delivery

Most procedures with Fentanyl involve other mode of delivery (injections) procedures are typically administered at high repeated dosages—ranging from 50 µgm to 150 µgm. Surprisingly it was determined from the dosage trials that even a small range dosage of 15-20 µgm of Fentanyl given over the vaginal mucosa are adequate for carrying out these gynecological procedures with good pain relief in a short time. This was unexpected because typically Fentanyl is administered at least 10 times higher dosage for chronic pain relief through intravenous injection.

Example 7: Human Studies

Human trials using the synergistic combination were carried out to determine the optimal dosage range that would provide the best results. Among the patients, Misoprostol was administered at dosages ranging from 0 µg to 200 µg and Fentanyl Solution is instilled at the same time at doses ranging from 0 µg to 20 µg vaginally. The combination could also be made into a gel or a pessary for vaginal insertion into the posterior Fornix. The various combinations of dosages and the results are tabulated (Table 1). The dosage was scored based on the criteria of level of bleeding, pain threshold and optimal dilation. The synergistic effect of the composition was observed after 60 minutes past administration. In some cases the synergistic effect of reducing pain and bleeding through numbness and dilation was observed even after 30-40 minutes.

Pain:

Pain relief is observed after 40 minutes of insertion of both drugs. Most of the patients had a good threshold for pain at Misoprostol dosage from 75 µg to 175 µg and Fentanyl Solution was administered at doses from 15 µgm to 20 µgm vaginally (0.3 ml to 0.4 ml). The synergistic effect of numbness, optimal dilation, lack of pain and bleeding was observed to last 2 to 3 hours after administration. The results of the dosage trial are tabulated (Table 1) below.

TABLE 1

Effect of Fentanyl and Misoprostol in various combinations with the tested subjects (No pain −, Pain +)

| Misoprostol (µgm) | Fentanyl (µgm) | | | | | | | | |
|---|---|---|---|---|---|---|---|---|---|
| | 0 | 3 | 5 | 7 | 9 | 12 | 15 | 17 | 20 |
| 0 | ++ | + | + | + | + | + | + | − | − |
| 25 | + | + | + | + | + | + | − | − | − |
| 50 | + | + | + | + | + | − | − | − | − |
| 75 | + | + | + | + | − | − | −− | −− | −− |
| 100 | + | + | + | − | − | − | −− | −− | −− |
| 125 | + | + | + | − | − | − | −− | −− | −− |
| 150 | + | + | − | − | − | − | −− | −− | −− |
| 175 | + | − | − | − | − | − | −− | −− | −− |
| 200 | + | + | + | + | + | + | − | − | − |

Cervix Dilation:

Cervix was found to be dilated to 5+ mm opening in human studies after 1½ to 2 hours. Optimal dilation combined with lack of pain makes the synergetic combination very useful for gynecological procedures like Hysterosalpingogram. Usually this procedure is very painful has failure rate of 30-40% under other drugs. The synergistic combination provides optimal dilation and pain free state after 30-40 minutes past administration. The effect lasts for about 1-2 hours which is sufficient time to perform most gynecological procedures that might have required general anesthesia. Therefore, other procedures like, hysteroscopy, diagnostic biopsy, polyp removal in uterus can also be satisfactory performed using these drug combinations.

What is claimed is:

1. A dilating device for unblocking a cervix pathway, the device comprising:
   (a) a shaft having a head at one end and a threaded part at the other end;
   (b) a base connected to the threaded part;
   (c) a taper part connected to the head;
   (d) a *Plantago ovata* attached to the taper part; and
   (e) a tubular structure, wherein the tubular structure covers the portion of the shaft between the base and the taper part.

2. The device of claim 1, wherein the shaft comprises at least one bore that runs through the shaft from the head to the threaded part.

3. The device of claim 2, wherein the at least one bore is configured to accomodate a feature selected from the group consisting of fluid transmission, a light source, a fluorescent probe, camera connectivity, a surgical probe, a drain to remove undesired liquid, and combinations thereof.

4. The device of claim 3, wherein the at least one bore can be used with a diagnostic solution used to flush the cervix.

5. The device of claim 4, wherein the diagnostic solution is selected from the group consisting of dilute acetic acid solution, radio contrast dye solution, and saline solution.

6. The device of claim 1, wherein the tubular structure comprises a bore sufficient to allow the shaft to pass through the tubular structure.

7. The device of claim 1, wherein the base is tubular insided with a threaded part and an unthreaded part.

8. The device of claim 1, wherein the taper part comprises a plurality of extensions configured to hold an attachment.

9. The device of claim 8, wherein the attachment is the *Plantago ovata* patch.

10. The device of claim 1, wherein the taper part has a bore through the center.

11. The device of claim 1, wherein the base has an external side that is tapered.

12. A dilating device for unblocking a cervix pathway, the device comprising:
 (a) a shaft having a head at one end and a threaded part at the other end;
 (b) a base connected to the threaded part;
 (c) a *Plantago ovata* cone connected to the head; and
 (d) a tubular structure, wherein the tubular structure covers the portion of the shaft between the base and the *Plantago ovata* cone.

13. The device of claim 12, wherein the shaft comprises at least one bore that runs through the shaft from the head to the threaded part.

14. The device of claim 13, wherein the at least one bore is configured to accomodate a feature selected from the group consisting of fluid transmission, a light source, a fluorescent probe, camera connectivity, a surgical probe, a drain to remove undesired liquid, and combinations thereof.

15. The device of claim 13, whererin the at least one bore can be used with a diagnostic solution used to flush the cervix.

16. The device of claim 15, wherein the diagnostic solution is selected from the group consisting of dilute acetic acid solution, radio contrast dye solution, and saline solution.

17. The device of claim 12, wherein the tubular structure comprises a bore sufficient to allow the shaft to pass through the tubular structure.

18. The device of claim 12, wherein the base is tubular inside with a threaded part and an unthreaded part.

19. The device of claim 12, wherein the base has an external side that is tapered.

* * * * *

UNITED STATES PATENT AND TRADEMARK OFFICE
CERTIFICATE OF CORRECTION

PATENT NO. : 10,933,057 B2
APPLICATION NO. : 16/026684
DATED : March 2, 2021
INVENTOR(S) : Pathyil Damoderam Krishna Kumar It is certified that error appears in the above-identified patent and that said Letters Patent is hereby corrected as shown below:

In the Claims

Column 20, Line 44 Claim 1:
Insert --patch-- after "ovata".

Column 20, Line 65 Claim 7:
Replace "insided" with --inside--.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*